US00PP16709P2

(12) United States Plant Patent
Monet

(10) Patent No.: US PP16,709 P2
(45) Date of Patent: Jun. 27, 2006

(54) NECTARINE TREE 'S 6816'

(50) Latin Name: *Prunus persica*
Varietal Denomination: S 6816

(75) Inventor: René Francois Monet, Villenave d'Ornon (FR)

(73) Assignee: Agri-Obtentions SA, Guyancourt Cedex (FR)

( * ) Notice: Subject to any disclaimer, the term of this patent is extended or adjusted under 35 U.S.C. 154(b) by 132 days.

(21) Appl. No.: 10/642,442

(22) Filed: Aug. 14, 2003

Related U.S. Application Data

(60) Provisional application No. 60/404,217, filed on Aug. 15, 2002.

(51) Int. Cl.
*A01H 5/00* (2006.01)

(52) U.S. Cl. ..... Plt./192

(58) Field of Classification Search ..... Plt./192, Plt./190
See application file for complete search history.

(56) References Cited

U.S. PATENT DOCUMENTS

PP12,008 P2 * 7/2001 Zaiger et al. ..... Plt./192

* cited by examiner

*Primary Examiner*—Anne Marie Grunberg
*Assistant Examiner*—June Hwu
(74) *Attorney, Agent, or Firm*—Stratton Ballew PLLC

(57) ABSTRACT

A new cultivar of nectarine tree (*Prunus persica* L. Batsch) named 'S 6816' is disclosed. The fruit of 'S 6816' is oblate, yellow fleshed, and freestone, and is notable for its early maturity and very sweet flavor.

6 Drawing Sheets

Latin name of the genus and species of the plant claimed: *Prunus persica* L. Batsch.
Variety denomination: 'S 6816'.

BACKGROUND OF THE INVENTION

The new nectarine tree 'S 6816' was developed by the Institut National de la Recherche Argonomique (INRA) at Angers, France, as part of a controlled breeding program. 'S 6816' was one of several seedlings resulting from a cross of [(Kiang-Si×Independence)×Summergrand]×Marsun (all unpatented). 'S 6816' was asexually propagated by budding at Angers, France, and has been observed to remain true to type over successive asexually propagated generations.

BRIEF SUMMARY OF THE INVENTION

'S 6816' was selected for its suitability as a commercial nectarine tree cultivar. Fruit of the 'S 6816' cultivar matures in late July in central Washington state, and is notable for its aromatic and sweet yellow flesh. The fruit of 'S 6816' is distinguishable from that of the parent varieties by its flat shape and smooth skin. The characteristics which distinguish 'S 6816' from its parents are set forth in Table 1.

TABLE 1

| Variety | Fruit Type | Shape | Flesh Color |
|---|---|---|---|
| S 6816 | Nectarine | Flat | Yellow |
| Kiang-Si | Peach | Flat | Yellow |
| Independence | Nectarine | Round | Yellow |
| Summergrand | Nectarine | Round | Yellow |
| Marsun | Peach | Round | Yellow |

This variety is distinguishable over related variety 'S 6817' (U.S. patent application Ser. No. 10/642,441) by its earlier maturity date and smaller and sweeter fruit.

BRIEF DESCRIPTION OF THE PHOTOGRAPHS

DETAILED BOTANICAL DESCRIPTION OF THE VARIETY

Figure 1:
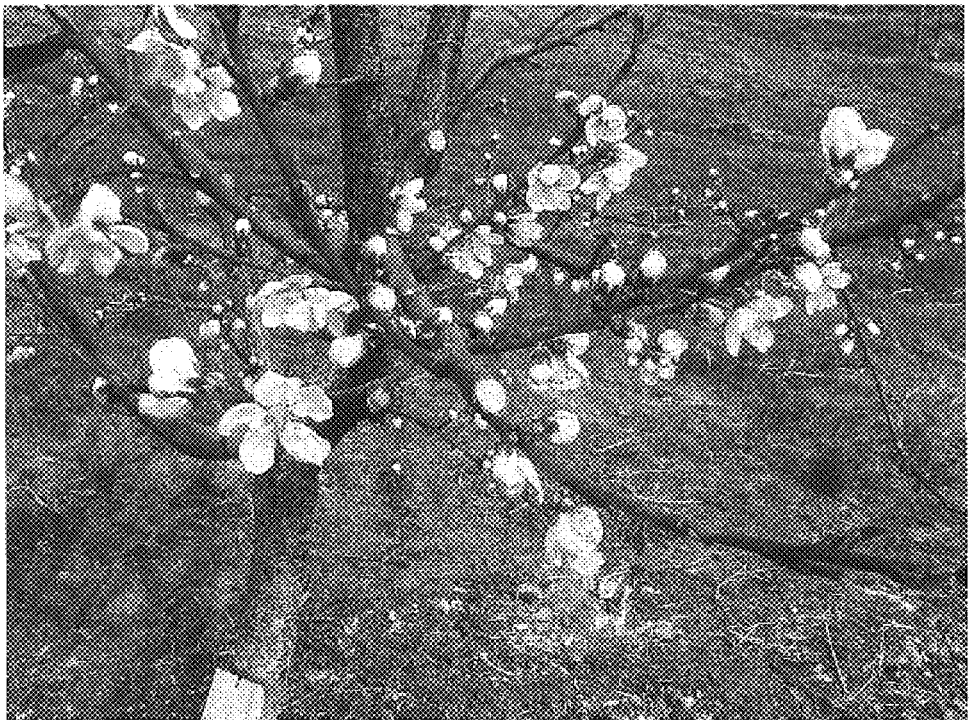
FIG. 1 shows branches and blossoms of the new cultivar.
Figure 2:
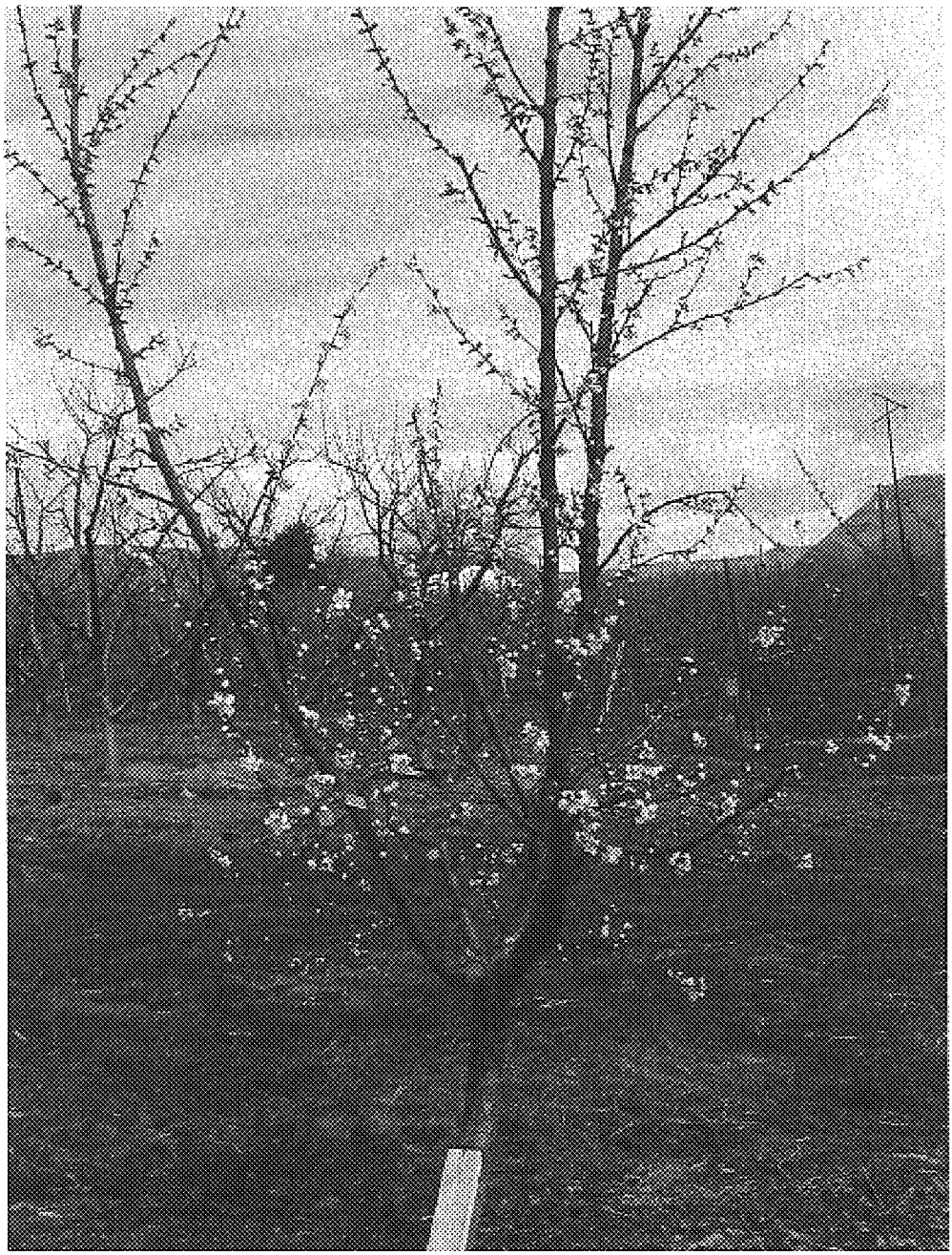
FIG. 2 shows a tree of the new cultivar.
Figure 3:
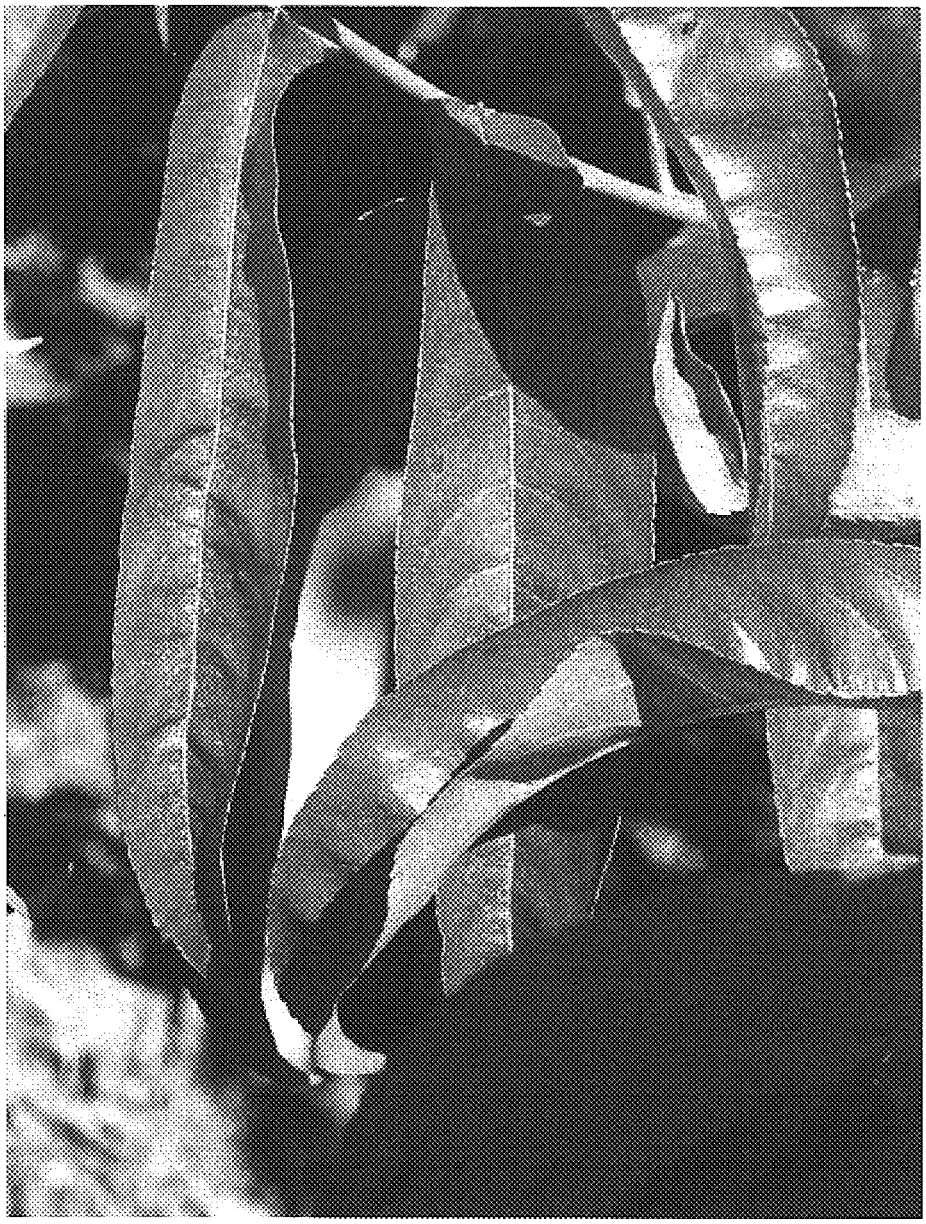
FIG. 3 shows leaves of the new cultivar.
Figure 4:
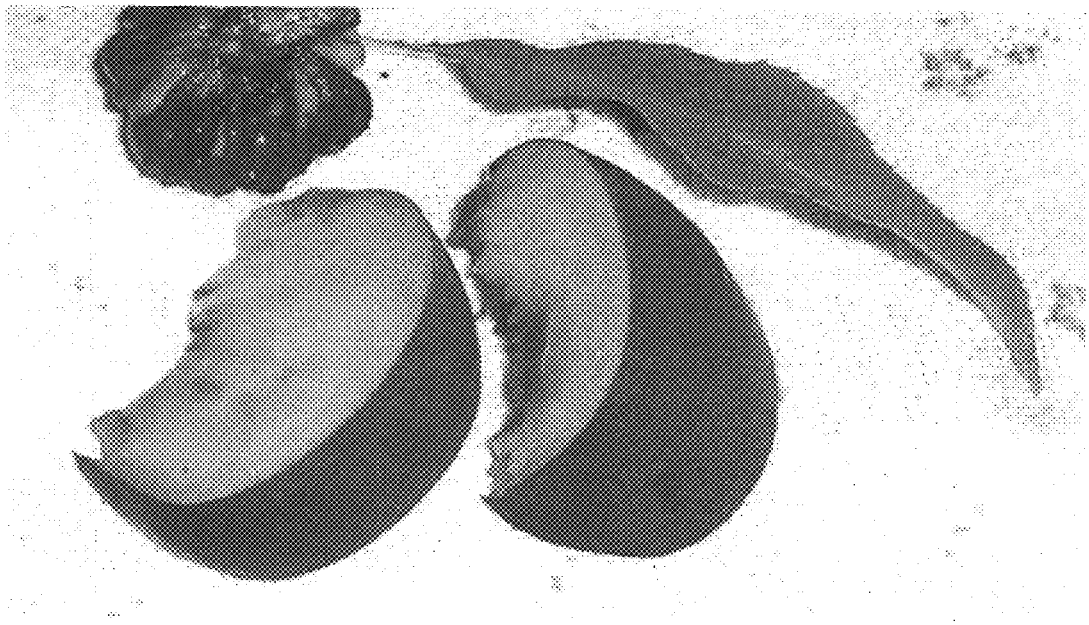
FIG. 4 shows a leaf, a stone, and a portion of a fruit of the new cultivar.
Figure 5:
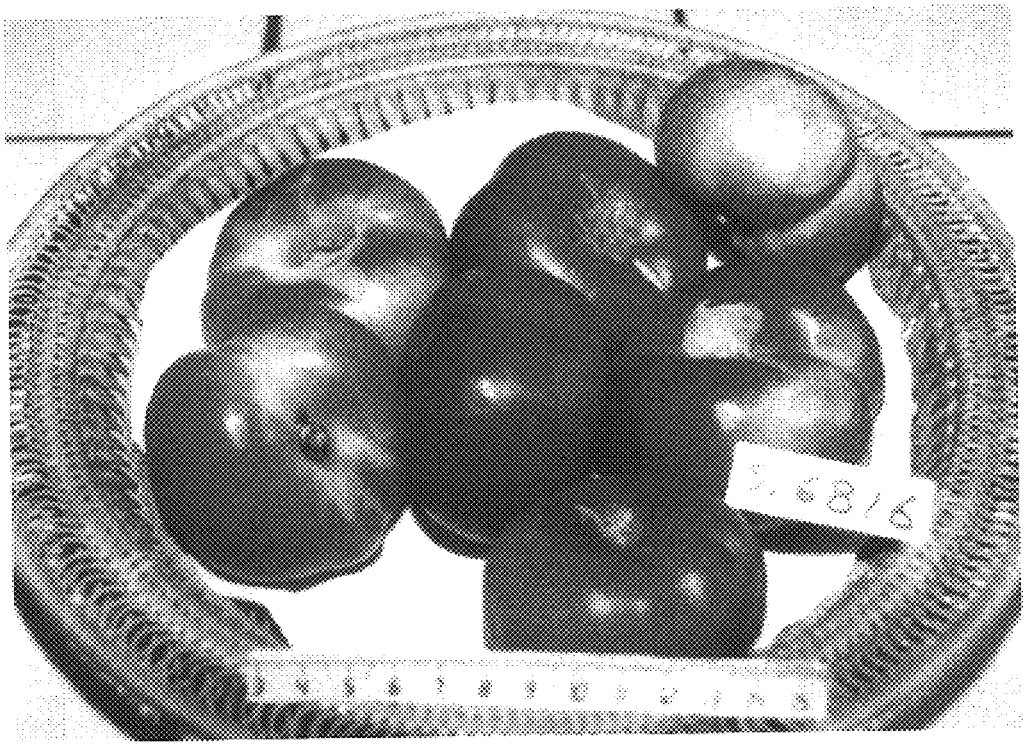
FIG. 5 shows fruit of the new cultivar.
Figure 6:
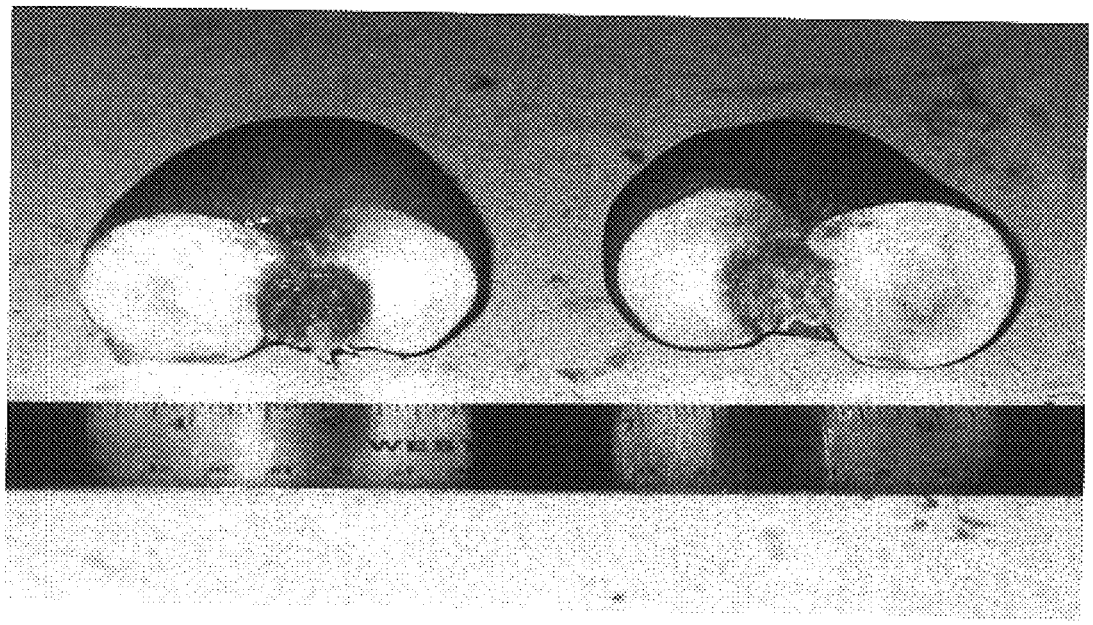
FIG. 6 shows a sectioned fruit of the new cultivar.

The following is a detailed botanical description of 'S 6816,' a new and distinct nectarine tree, based on observations made during the 2004 growing season, of specimens planted at Parker, Wash., USA, in 1999. The described trees were grown on 'Lovell' (not patented) rootstock. All colors are described according to The Royal Horticultural Society Color Chart. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Size.*—Large, width 2.2 m wide, height 3.4 m.
*Vigor.*—Strong.
*Habit.*—Upright.
*Trunk.*—Diameter 31 cm at soil level; very rough; overcolor grey 201D; undercolor grey 175A; lenticels prominent, 0.3 to 0.5 cm, yellow 159A.

*Branches.*—Smooth, greyed red 181A, internode length 3.1 to 3.8 cm, lateral branch diameter 1.8 cm, length 46.2 cm (previous season growth).

Leaves:

*Young shoot — length of stipule.*—Medium.

*Size.*—Length 10.5 cm; 4.0 cm.

*Ratio length to width.*—Medium.

*Shape.*—Lanceolate, base rounded, apex acuminate, recurved, cross section concave.

*Color.*—Upper surface green 146A, lower surface green N144A, upper venation color green 154D.

*Texture.*—Smooth.

*Margin.*—Serrate to serrulate.

Petiole:

*Size.*—Length 1.5 cm, diameter 0.2 cm.

*Color.*—Green 154D.

*Glands.*—Present, usually 2, reniform.

Flowers:

*Bud.*—Length 0.9 to 1.1 cm, round, smooth, hardy, red-purple 59A, tip pink 62A.

*Bud burst.*—March 18 at Parker, Wash.

*Bloom period.*—March 18 to April 7 at Parker, Wash.

*Flower type.*—Showy, fragrant, 1 to 4 per cluster.

*Petals.*—Quantity 5; length 1.8 to 2.1 cm, width 1.3 to 1.5 cm; margins ruffled, overlapping; shape obovate to rotund; color pink 69A.

*Sepals.*—Length 0.5 to 0.6 cm; width 0.4 to 0.5 cm; color red-purple 59A.

*Flower size.*—Diameter 3.5 to 3.7 cm.

*Reproductive organs.*—Stamen white 155D, quantity 39, length 1.0 to 1.3 cm; anther length 0.5 cm, brown 199A; filament 0.9 to 1.2 cm; pistil 0.9 to 1.0 cm, smooth, yellow 3A.

*Pollen.*—Scarce, yellow 1A.

Fruit:

*Size.*—Small, diameter 70 mm, height 4.0 cm.

*Shape* (*ventral view*).—Broad oblate.

*Shape of pistil end.*—Weakly depressed.

*Symmetry.*—Symmetric.

*Prominence of suture.*—Weak.

*Depth of stalk cavity.*—Shallow, 0.5 cm.

*Width of stalk cavity.*—Broad, 2.8 cm.

*Skin.*—Color: ground color orange-red 34C, over color red-purple 59A; thin, smooth, tenacious.

*Pubescence.*—Absent.

*Firmness of flesh.*—Soft.

*Ground color of flesh.*—Yellow-orange 17C.

*Anthocyanin coloration directly under skin.*—Absent or very weakly expressed.

*Anthocyanin coloration of flesh.*—Absent or very weakly expressed.

*Anthocyanin coloration around stone.*—Present, red-purple 59C.

*Pit cavity.*—Diameter 3.0 cm, color red-purple 59C.

*Texture of flesh.*—Not fibrous.

*Sweetness.*—Very sweet, 12° Brix.

*Acidity.*—Low.

Stone:

*Size.*—Small, diameter 3.0 cm.

*Shape in lateral view.*—Oblate.

*Color.*—Red-purple 59C.

*Relief of surface.*—Small pits, ridges.

*Tendency of splitting at peak harvest.*—Absent or very low.

*Adherence to flesh.*—Absent (freestone).

Time of maturity for consumption: Early, late July in Parker, Wash.

Tendency to preharvest drop: Absent or very weak.

Resistance to diseases and pests: None observed.

Heat and cold tolerance: Tolerant in area tested (USDA Zone 6).

We claim:

1. A new and distinct nectarine tree, substantially as shown and described herein.

* * * * *